(12) United States Patent
Isaacson

(10) Patent No.: US 12,083,290 B2
(45) Date of Patent: Sep. 10, 2024

(54) CATHETER ASSEMBLY CLAMP HAVING AN ACOUSTIC SENSOR

(71) Applicant: Becton, Dickinson and Company, Franklin Lakes, NJ (US)

(72) Inventor: S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 567 days.

(21) Appl. No.: 16/841,341

(22) Filed: Apr. 6, 2020

(65) Prior Publication Data

US 2020/0316344 A1 Oct. 8, 2020

Related U.S. Application Data

(60) Provisional application No. 62/830,847, filed on Apr. 8, 2019.

(51) Int. Cl.
  *A61M 25/02* (2006.01)
  *G16H 10/60* (2018.01)

(52) U.S. Cl.
  CPC ....... *A61M 25/02* (2013.01); *A61M 2025/024* (2013.01); *A61M 2205/18* (2013.01); *A61M 2205/3331* (2013.01); *A61M 2205/3375* (2013.01); *G16H 10/60* (2018.01)

(58) Field of Classification Search
  CPC ............ A61M 25/02; A61M 2025/024; A61M 2205/18; A61M 2205/3331; A61M 2205/3375; G16H 10/60

USPC .......................................................... 604/65
See application file for complete search history.

(56) References Cited

U.S. PATENT DOCUMENTS

| | | | |
|---|---|---|---|
| 2002/0136662 A1* | 9/2002 | Myrick | ............. B01F 23/23413 422/45 |
| 2010/0228269 A1 | 9/2010 | Garrison et al. | |
| 2016/0206809 A1* | 7/2016 | Kamen | ............. A61B 5/150022 |
| 2017/0120040 A1* | 5/2017 | Burkholz | ............. A61M 39/284 |

FOREIGN PATENT DOCUMENTS

| | | |
|---|---|---|
| CN | 107823754 | 3/2018 |
| JP | 2015510407 A | 4/2015 |
| JP | 2017113144 A | 6/2017 |

* cited by examiner

*Primary Examiner* — Phillip A Gray
(74) *Attorney, Agent, or Firm* — Kirton McConkie; Whitney Blair; Kevin Stinger

(57) ABSTRACT

A method to manage flushing of a catheter assembly a clamp configured to clamp an extension tube of a catheter assembly. The clamp may include an acoustic sensor configured to detect fluid flowing through the extension tube. The clamp and the acoustic sensor may be disposed outside of the extension tube. The clamp may include a pinch clamp or a non-pinch clamp. The acoustic sensor may be embedded in the clamp. The method may include detecting, via the acoustic sensor, fluid flowing through the extension tube.

14 Claims, 7 Drawing Sheets

CATHETER ASSEMBLY CLAMP HAVING AN ACOUSTIC SENSOR

RELATED APPLICATIONS

This application claims the benefit of U.S. Application No. 62/830,847, filed Apr. 8, 2019, and entitled CATHETER ASSEMBLY CLAMP HAVING AN ACOUSTIC SENSOR, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral IV catheter ("PIVC"), a peripherally inserted central catheter ("PICC"), or a midline catheter. As its name implies, the over-the-needle catheter may be mounted over an introducer needle having a sharp distal tip. The sharp distal tip may be used to pierce skin and the vasculature of the patient. Insertion of the catheter into the vasculature may follow the piercing of the vasculature by the needle. The needle and the catheter are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the catheter in place for future blood withdrawal and/or fluid infusion.

In some instances, the catheter may become unusable or compromised be due to occlusion of the catheter over time. In response to the catheter becoming occluded, the catheter may need to be removed and replaced with a new catheter. Catheter occlusions may be thrombotic, resulting from formation of a thrombus within or surrounding a distal tip of the catheter. Catheter occlusions may also be non-thrombotic, resulting from precipitates, mechanical obstructions, and other factors. Further, catheter occlusions can lead to catheter infection, pulmonary embolism, post-thrombotic syndrome, and other negative health outcomes. Clinicians may regularly flush the catheter to prevent occlusion and extend an indwelling period of the catheter.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In some embodiments, a method to manage flushing of a catheter assembly may include providing a clamp for an extension tube of the catheter assembly. In some embodiments, the clamp may include an acoustic sensor, which may be configured to detect the clamp is open or fluid is flowing through the extension tube of the catheter assembly. In some embodiments, the acoustic sensor may be configured to detect the clamp is closed or fluid is not flowing through the extension tube of the catheter assembly.

In some embodiments, the method may include starting a timer in response to the acoustic sensor detecting the clamp is closed. In some embodiments, the method may include providing an alert in response to the timer reaching a predetermined duration of time. In some embodiments, the alert may indicate to a clinician that the catheter assembly should be opened and flushed, which may prevent occlusion of the catheter assembly.

In some embodiments, providing the alert may include transmitting an alert signal over a network to a monitoring device, such as a clinician monitoring device. In some embodiments, the alert signal may indicate to the monitoring device to provide the alert. In some embodiments, the alert may include a sound, a tactile vibration, or a visual cue. In some embodiments, the visual cue may include a change in status of a light. In some embodiments, an indication may be provided in an electronic health record of a patient in response to the acoustic sensor detecting the clamp is closed.

In some embodiments, the acoustic sensor may be configured to detect the clamp is open. In some embodiments, in response to the acoustic sensor detecting the clamp is open for another predetermined duration of time, the timer may be stopped and/or reset. In some embodiments, in response to the acoustic sensor detecting the clamp is open for the other predetermined duration of time, another alert signal may be transmitted over the network to the monitoring device to stop the alert or provide another alert. In some embodiments, another indication may be provided in the electronic health record of the patient in response to the acoustic sensor detecting the clamp is open for the other predetermined duration of time.

In some embodiments, another acoustic sensor may be provided. In some embodiments, the acoustic sensor and the other acoustic sensor may provide a robust determination of whether fluid is flowing through the extension tube and the clamp is open or closed. In some embodiments, the acoustic sensor may be disposed distal to the other acoustic sensor. In some embodiments, a fluid flow direction within the extension tube may be determined in response to the acoustic sensor detecting fluid flowing through the extension tube prior to or after the other acoustic sensor detecting fluid flowing through the extension tube. In some embodiments, in response to the other acoustic sensor detecting the clamp is open and fluid is flowing through the extension tube of the catheter assembly, the timer may be stopped and/or reset.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
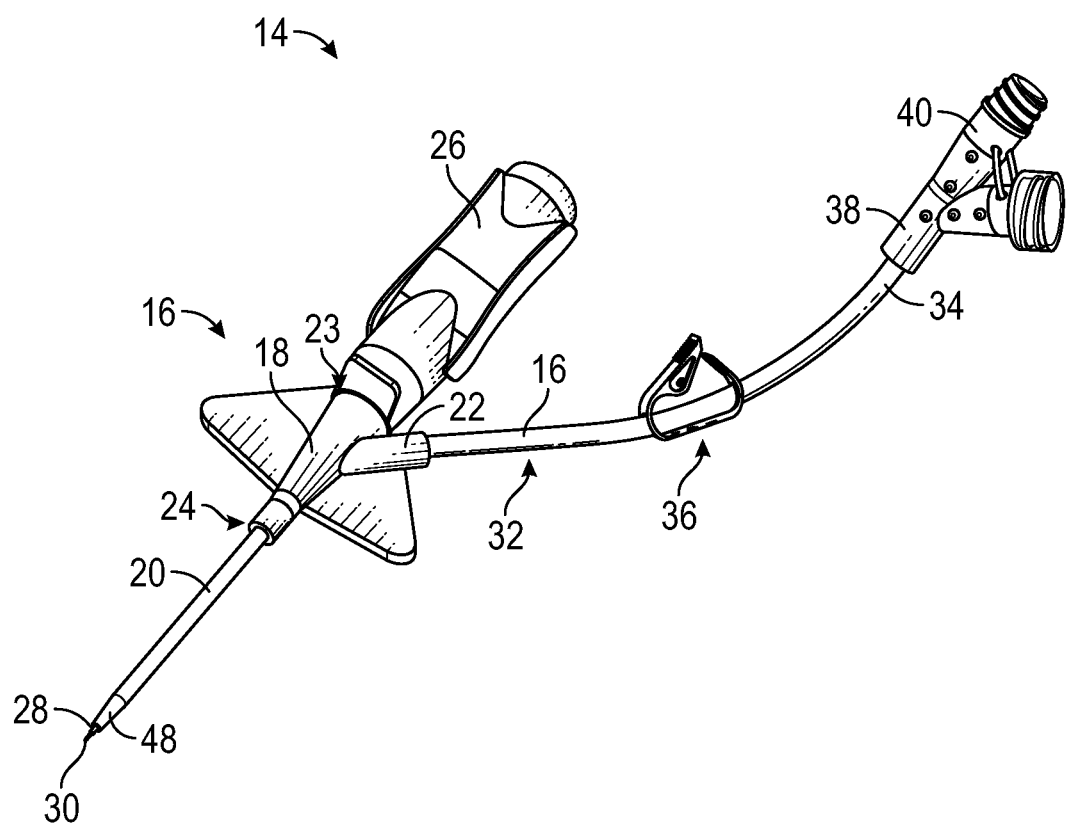
FIG. 1A is a an upper perspective view of an example catheter system, according to some embodiments.

Referring now to FIG. 1A, an example catheter system 14 is illustrated, according to some embodiments. In some embodiments, the catheter system 14 may include a catheter assembly 16. In some embodiments, the catheter assembly 16 may include a catheter adapter 18 and a catheter 20 extending distally from the catheter adapter 18. In some embodiments, the catheter adapter 18 may include a side port 22 in fluid communication with the lumen of the catheter adapter 18. In some embodiments, the catheter adapter 18 may include a proximal end 23, a distal end 24, and a lumen extending there between. In some embodiments, the catheter 20 may include a PIVC.

In some embodiments, the catheter assembly 16 may be removably coupled to a needle assembly, which may include a needle hub 26 and an introducer needle 28. In some embodiments, the introducer needle 28 may include a sharp distal tip 30. In some embodiments, a proximal end of the introducer needle 28 may be secured within the needle hub 26.

In some embodiments, the introducer needle 28 may extend through the catheter 20 when the catheter assembly 16 is in an insertion position ready for insertion into vasculature of a patient, as illustrated, for example, in FIG. 1A. In some embodiments, in response to the introducer needle 28 being inserted into the vasculature of the patient, flashback of blood may flow through the sharp distal tip 30 of the introducer needle 28 and may be visible to a clinician between the introducer needle 28 and the catheter 20 and/or at another location within the catheter assembly 16.

In some embodiments, in response to confirmation via the blood flashback that the catheter 20 is positioned within vasculature of the patient, the needle assembly may be removed from the catheter assembly 16. In some embodiments, when the needle assembly is coupled to the catheter assembly 16, as illustrated, for example, in FIG. 1A, the introducer needle 28 of the needle assembly may extend through a septum disposed within the lumen of the catheter adapter 18.

In some embodiments, the catheter system 14 may include a catheter line 32, which may include an extension tube 34 and a clamp 36 through which the extension tube 34 may extend. In some embodiments, a distal end of the extension tube 34 may be integrated with the catheter adapter 18, as illustrated, for example, in FIG. 1A. For example, the extension tube 34 may be integrated with the side port 24 of the catheter adapter 18. In some embodiments, the extension tube 34 may be removably coupled to the catheter adapter 18. In some embodiments, the clamp 36 may selectively close off the extension tube 34 to prevent blood or another fluid from flowing through the extension tube 34.

In some embodiments, an adapter 38 may be coupled to a proximal end of the extension tube 34. In some embodiments, the adapter 38 may include a Y-adapter or another suitable connector. In some embodiments, a needleless connector 40 may be coupled to the adapter 38. In some embodiments, the adapter 38 and/or the needleless connector 40 may be used to connect the catheter 20 with a medical device for fluid administration or blood withdrawal. The medical device may include a transfusion bag, syringe, or any other suitable medical device.

In some embodiments, the catheter system 14 may include any suitable catheter assembly 16 and the clamp 36 may be coupled to any suitable extension tube. In some embodiments, the extension tube 34 may extend from the proximal end 23 of the catheter adapter 18. In some embodiments, the clamp 36 may be disposed on an IV line, which may extend between an IV bag and the catheter assembly 16. In some embodiments, the catheter assembly 16 may include a PIVC, a PICC, or a midline catheter. In some embodiments, a peripherally inserted central catheter ("PICC") assembly may include pigtail extension tubes, and a particular clamp 36 may be coupled to one or more of the pigtail extension tubes.

In some embodiments, an extension set may be configured to directly or indirectly couple to the catheter assembly 16. In some embodiments, the extension set may include the IV line, the extension tube 34, or any other extension tube in fluid communication with the catheter assembly 16. In some embodiments, the extension set may include the clamp 36.

Figure 1B:
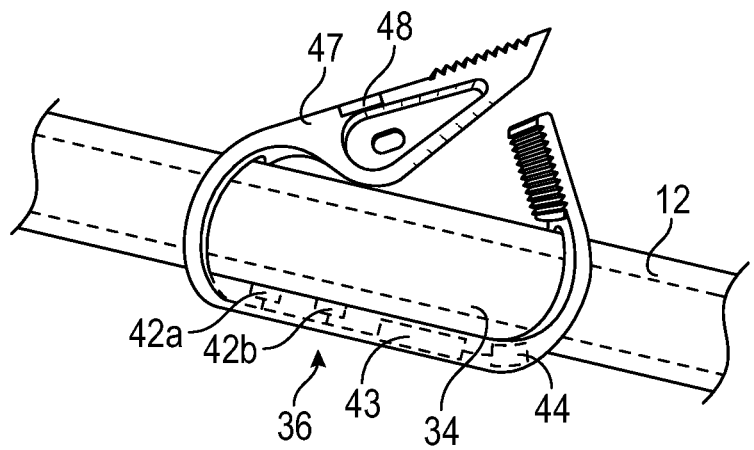
FIG. 1B is an upper perspective view of an example clamp, illustrating the clamp in an open position, according to some embodiments.

Referring now to FIG. 1B, in response to the clamp 36 being opened, fluid may flow through the extension tube 34 and the catheter assembly 16. For example, fluid may be infused into the patient via a medical device coupled to the adapter 38 or blood may be withdrawn from the patient into a blood collection device coupled to the adapter 38. In some embodiments, the clamp 36 may include a first acoustic sensor 42a and/or a second acoustic sensor 42b (which may be collectively referred to in the present disclosure as "acoustic sensors 42"). In some embodiments, each of the acoustic sensors 42 may be configured to detect fluid is flowing through the extension tube 34 or the clamp 36 is open. In some embodiments, each of the acoustic sensors 42 may be configured to detect fluid is not flowing through the extension tube 34 or the clamp 36 is closed. In some embodiments, the first acoustic sensor 42a and/or the second acoustic sensor 42b may include one or more microphones.

In some embodiments, the first acoustic sensor 42a and the second acoustic sensor 42b may provide a robust determination of whether fluid is flowing through the extension tube 34 and the clamp 36 is open or closed. In some embodiments, the first acoustic sensor 42a may be disposed distal to the second acoustic sensor 42b. In some embodiments, a fluid flow direction within the extension tube 34 may be determined in response to the first acoustic sensor 42a detecting fluid flowing through the extension tube 34 prior to or after the other acoustic sensor 42b detecting fluid flowing through the extension tube 34. In some embodiments, the fluid flow direction may be determined to be proximal in response to the first acoustic sensor 42a detecting fluid flowing through the extension tube 34 prior to the second acoustic sensor 42b detecting fluid flowing through the extension tube 34. In some embodiments, the fluid flow direction may be determined to be distal in response to the second acoustic sensor 42b detecting fluid flowing through the extension tube 34 prior to the first acoustic sensor 42a.

In some embodiments, the acoustic sensors 42 may be electrically coupled to a circuit board 43 and a battery 44. In some embodiments, a location of the circuit board 43 and the battery 44 may vary. In some embodiments, the circuit board 43 may include a communication unit.

Figure 1C:
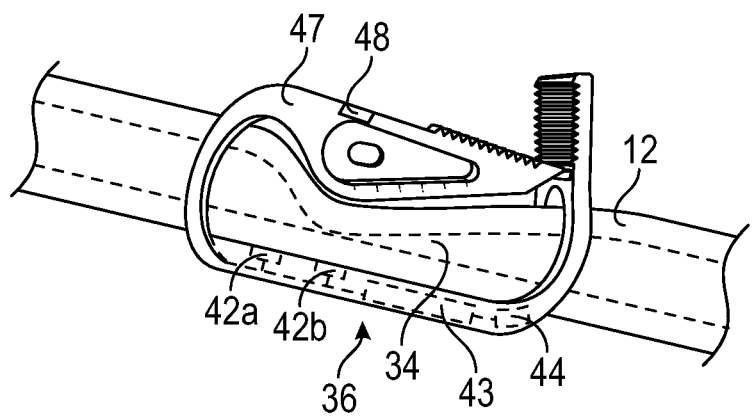
FIG. 1C is an upper perspective view of the clamp of FIG. 1B, illustrating the clamp is a closed position, according to some embodiments.

Referring now to FIG. 1C, in response to the clamp 36 being closed, fluid may be prevented from flowing through the extension tube 34. In some embodiments, in response to the clamp 36 being closed, substantially all fluid may be prevented from flow through the extension tube 34. In some embodiments, the clamp 36 may include a pinch clamp, which may pinch the extension tube 34 in response to movement of the clamp 36 to the closed position.

In some embodiments, the clamp 36 may include any clamp that is coupled with an extension tube, such as, for example, the extension tube 34. In some embodiments, an example clamp 36 is described in U.S. patent application Ser. No. 15/286,248, filed Oct. 5, 2016, entitled "PINCH CLAMP DEVICE," which is hereby incorporated by reference in its entirety. In some embodiments, the extension tube 34 may extend through the clamp 36. In some embodiments, the clamp 36 may include an arm 47, which may include a protrusion that contacts and pinches the extension tube 34. In some embodiments, the clamp 36 may include any suitable clamp, and the acoustic sensors 42 may include any suitable acoustic sensors. In some embodiments, the acoustic sensors 42 may be disposed at various locations.

In some embodiments, the acoustic sensors 42 may be embedded in the clamp 36. In these and other embodiments, one or more of the acoustic sensors 42 may contact the extension tubing 34. In some embodiments, one or more of the acoustic sensors 42 may be spaced apart from the extension tubing 34. In some embodiments, the first acoustic sensor 42a may be disposed distal to the second acoustic sensor 42b.

In some embodiments, a position of the acoustic sensors 42 may vary. In some embodiments, the acoustic sensors 42 may be disposed on a clamping surface of the clamp 36 that contacts the extension tube 34 when the clamp 36 is in an open position and/or a closed position. In some embodiments, the clamping surface may be generally planar or curved. In some embodiments, the acoustic sensors 42 may be disposed on a non-clamping surface. In some embodiments, the acoustic sensors 42 may be disposed on opposite sides of the extension tube 34. In some embodiments, the acoustic sensors 42 may be disposed on a same side of the extension tube 34.

In some embodiments, the clamp 36 may provide an alert which may include a sound, a tactile vibration, or a visual cue. In some embodiments, the visual cue may include a change in status of a light. FIGS. 1B-1C illustrate an example light 48, according to some embodiments. In some embodiments, the status of the light 48 may change in response to the clamp 36 being closed for a predetermined duration of time. For example, the light 48 may turn on or may change color in response to the clamp 36 being closed for the predetermined duration of time. As another example, the light 38 may blink or change a rate of blinking in response to the clamp 36 being closed for the predetermined duration of time.

In some embodiments, the predetermined duration of time may correspond to a time prior to a clinically recommended time to flush the catheter assembly 16. In these embodiments, the alert may include a warning, which may indicate to the clinician that a clinically recommended time to flush the catheter assembly 16 is approaching. In some embodiments, the clinically recommended time to flush the catheter assembly 16 may be between about 6 hours and about 8 hours from the previous flushing of the catheter assembly 16.

In some embodiments, the predetermined duration of time may correspond to the clinically recommended time to flush the catheter assembly 16. In some embodiments, a first alert may be provided by the clamp 36 in response to the clinically recommended time to flush the catheter assembly 16 approaching (such as, for example, in 30 minutes, 10 minutes, or 5 minutes), and a second alert may be provided by the clamp 36 in response to arrival of the clinically recommended time to flush the catheter assembly 16. In some embodiments, the first alert may include a yellow or orange light, and the second alert may include a red light.

In some embodiments, the light 48 may be disposed at various locations on the clamp 36, which may be visible to the clinician. In some embodiments, the clamp 36 may include multiple lights 48. In some embodiments, a size of the light 48 may vary.

Figure 2A:
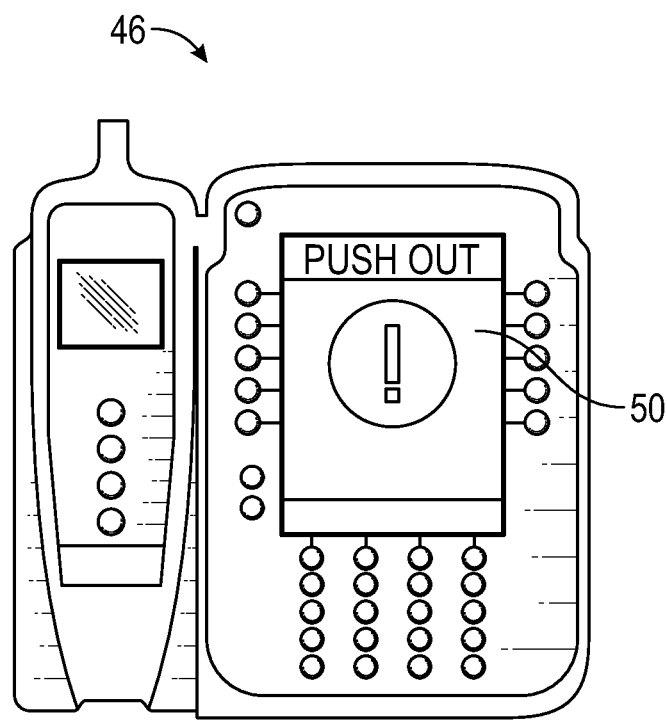
FIG. 2A is an upper perspective view of an example clinician monitoring device, according to some embodiments.

Referring now to FIG. 2A, an example clinician monitoring device 46 is illustrated, according to some embodiments. Examples of the clinician monitoring device 46 may include a computing device, a mobile phone, a smartphone, a tablet computer, a laptop computer, a desktop computer, a medical device, or a connected device (e.g., a smartwatch, smart glasses, or any other connected device). In some embodiments, in addition to the clamp 36 or as an alternative to the clamp 36, the clinician monitoring device 46 may provide the alert.

In some embodiments, the clinician monitoring device 46 may include a display screen 50, which may provide the alert. In some embodiments, the alert may include a phrase such as, for example, "Flush Due." In some embodiments, the alert may include a visual cue on the display screen 50, such as a portion of the display screen 50 that lights up or changes color. In some embodiments, the portion of the display screen 50 may blink or change a rate of blinking to provide the alert. In some embodiments, the clinician monitoring device 46 may include the light 48, as described, for example, with respect to FIG. 1C.

Figure 2B:
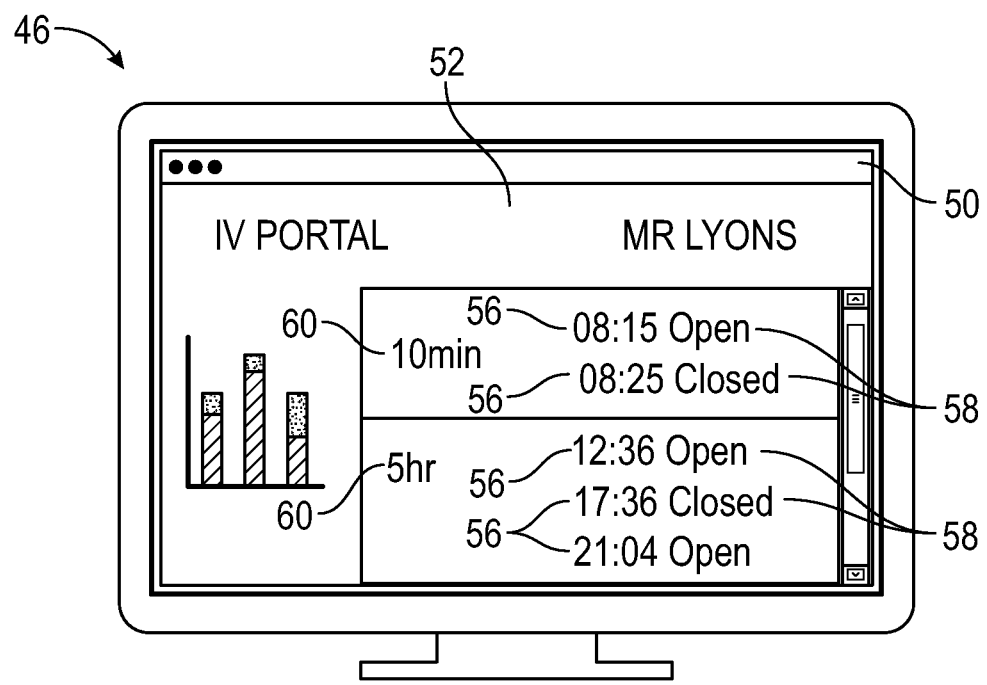
FIG. 2B is an example electronic health record that may be presented on a display screen of a clinician monitoring device, according to some embodiments.

Referring now to FIG. 2B, an example electronic health record 52 that may be presented on the display screen 50 of the clinician monitoring device 46 is illustrated, according to some embodiments. In some embodiments, an indication may be provided on the display screen 50 in response to opening and/or closing of the clamp 36. In some embodiments, the indication may be provided on the display screen 50 in response to opening the clamp 36 for a particular predetermined duration of time and/or closing the clamp 36 for a particular predetermined duration of time.

In some embodiments, the indication may include one or more of the following: a time of day 56, a status 58, and a duration of time 60. In some embodiments, the duration of time 60 may include a duration of time the clamp 36 has been closed. In some embodiments, the status 58 may include "open" and may be adjacent to the time of day 56, indicating to the clinician the time of day at which the clamp 36 was opened. In some embodiments, the status 58 may include "closed" and may be adjacent to the time of day 56, indicating to the clinician the time of day at which the clamp 36 was closed.

Figure 3:
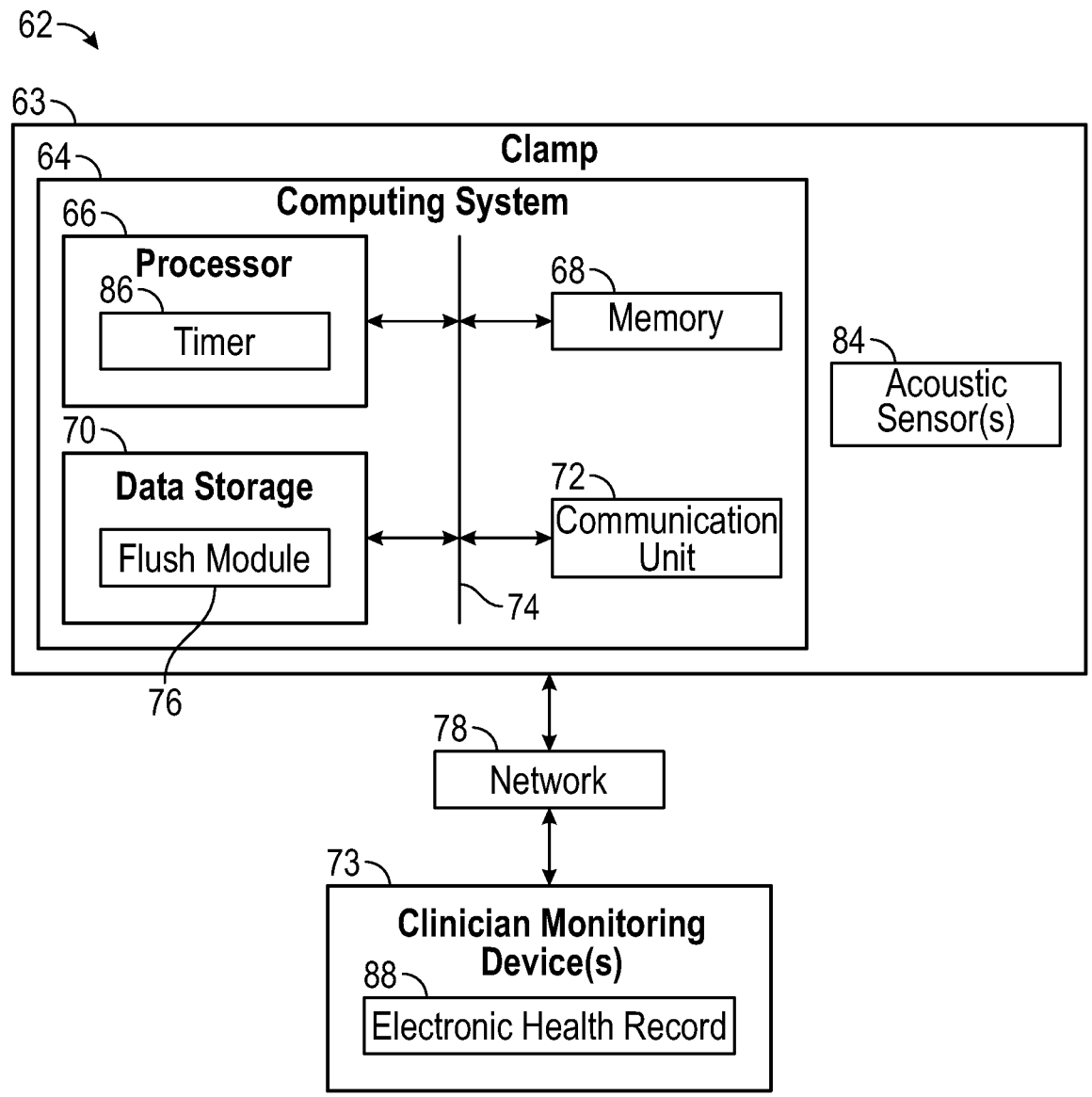
FIG. 3 is a block diagram of an example flush management system, according to some embodiments.

FIG. 3 is as block diagram of an example flush management system (FM system) 62, arranged in accordance with at least one embodiment described in the present disclosure.

In some embodiments, the FM system 62 may include the clamp 63. In some embodiments, the clamp 63 may include or correspond to the clamp 36 described with respect to FIG. 1 or the clamp 90 described with respect to FIG. 4. In some embodiments, the clamp 63 may include a computing system 64.

In some embodiments, the computing system 64 may include a processor 66, a memory 68, a data storage 70, and a communication unit 72. In some embodiments, the processor 66, the memory 68, the data storage 70, and the communication unit 72 may be communicatively coupled by a bus 74. The bus 74 may include, but is not limited to, a controller area network (CAN) bus, a memory bus, a storage interface bus, a bus/interface controller, an interface bus, or the like or any combination thereof. In some embodiments, the processor 66 may include a timer 75. In some embodiments, the timer 75 may be a separate component linked to the processor 66.

In general, the processor 66 may include any suitable special-purpose or general-purpose computer, computing entity, or processing device including various computer hardware or software modules and may be configured to execute instructions stored on any applicable computer-readable storage media. For example, the processor 66 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 3, the processor 66 may include any number of processors configured to perform, individually or collectively, any number of operations described in the present disclosure. Additionally, one or more of the processors 66 may be present on one or more different electronic devices.

In some embodiments, the processor 66 may interpret and/or execute program instructions and/or process data stored in the memory 68, the data storage 70, or the memory 68 and the data storage 70. In some embodiments, the processor 66 may fetch program instructions from the data storage 70 and load the program instructions in the memory 68. In some embodiments, after the program instructions are loaded into memory 68, the processor 66 may execute the program instructions.

For example, in some embodiments, a flush module 76 may be included in the data storage 70 as program instructions. In some embodiments, the flush module 76 may be configured to manage flushing of the catheter line 32 and the catheter assembly 16. In some embodiments, the flush module 76 may be configured to monitor fluid flow through the catheter assembly 16. The processor 66 may fetch the program instructions of the flush module 76 from the data storage 70 and may load the program instructions of the flush module 76 in the memory 68. After the program instructions of the flush module 76 are loaded into the memory 68, the processor 66 may execute the program instructions such that the computing system 64 may implement the operations associated with the flush module 76 as directed by the instructions.

The memory 68 and the data storage 70 may include computer-readable storage media for carrying or having computer-executable instructions or data structures stored thereon. Such computer-readable storage media may include any available media that may be accessed by a general-purpose or special-purpose computer, such as the processor 66. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 66 to perform a certain operation or group of operations.

In some embodiments, one or more clinician monitoring devices 73 may be connected to the computing system 64 via a network 78. In these and other embodiments, the network 78 may include a wired or wireless network, and may have any suitable configuration, such as a star configuration, a token ring configuration, or other configurations. Furthermore, in some embodiments, the network 78 may include an Ethernet network, a local area network (LAN), a wide area network (WAN) (e.g., the Internet), and/or other interconnected data paths across which multiple devices may communicate. In some embodiments, the network 78 may include a peer-to-peer network. In some embodiments, the network 78 may also be coupled to or include portions of a telecommunications network that may enable communication of data in a variety of different communication protocols. In some embodiments, the clinician monitoring devices 73 may include or correspond to any of the clinician monitoring devices 46 described with respect to FIG. 2.

In some embodiments, the network 78 may include BLUETOOTH® communication networks and/or cellular communications networks for sending and receiving data including via short messaging service (SMS), multimedia messaging service (MMS), hypertext transfer protocol (HTTP), direct data connection, wireless application protocol (WAP), e-mail, etc. The network 78 may enable communication via a standard-based protocol such as smart energy profile (SEP), Echonet Lite, OpenADR, or another suitable protocol (e.g., wireless fidelity (Wi-Fi), ZigBee, HomePlug Green, etc.).

In some embodiments, the communication unit 72 may be configured to transmit data to and receive data from the clinician monitoring devices 73 via the network 78. In some embodiments, the communication unit 72 may also be configured to transmit and receive data from a display screen 80 and/or an electronic health record 82. In some embodiments, the display screen 80 may include or correspond to the display screen 50 described with respect to FIG. 2A or 2B. In some embodiments, the electronic health record 82 may include or correspond to the electronic health record 52 of FIG. 2B. In some embodiments, the flush module 76 may be configured to send and receive data via the communication unit 72.

In some embodiments, the communication unit 72 may include a port for direct physical connection to the network 78 and/or another communication channel. For example, the communication unit 72 may include a universal serial bus (USB) port, a secure digital (SD) port, a category 5 cable (CAT-5) port, or similar port for wired communication with another device. In some embodiments, the communication unit 72 may include a wireless transceiver for exchanging data with the clinician monitoring device 46 or other communication channels using one or more wireless communication methods, including IEEE 802.11, IEEE 802.16, BLUETOOTH®, or another suitable wireless communication method.

In some embodiments, the communication unit 72 may include a cellular communications transceiver for sending and receiving data over a cellular communications network including via SMS, MMS, HTTP, direct data connection, WAP, e-mail, or another suitable type of electronic communication. The communication unit 72 may also provide other conventional connections to the network 78 for distribution of files or media objects using standard network protocols including transmission control protocol/internet protocol (TCP/IP), HTTP, HTTP secure (HTTPS), and simple mail transfer protocol (SMTP).

An example of how the flush module 76 may manage flushing of a catheter assembly or monitor fluid flow through the catheter assembly is now provided. In some embodiments, in response to one or more acoustic sensors 84 detecting the clamp is closed, the flush module 76 may be configured to start a timer 86. In some embodiments, the acoustic sensors 84 may include or correspond to the acoustic sensors 42 described with respect to FIG. 1 or 4. In some embodiments, in response to the timer 86 reaching a predetermined duration of time, the flush module 76 may be configured to generate one or more alerts at the clamp and/or to transmit an alert signal over the network 78 to the clinician monitoring devices 73, which may provide one or more alerts. In some embodiments, the alerts may include any of the alerts described with respect to FIGS. 1 and 2. In some embodiments, the alerts may indicate to the clinician that the clinically recommended time to flush the catheter assembly has arrived or is approaching.

In some embodiments, the flush module 76 may be configured to provide an indication in an electronic health record 88 of a patient in response to the acoustic sensors 84 detecting the clamp 63 is closed. In some embodiments, the electronic health record 88 may be stored and/or displayed on the clinician monitoring devices 73. In some embodiments, the electronic health record 88 may include or correspond to the electronic health record 52 described with respect to FIG. 2.

In some embodiments, in response to the acoustic sensors 84 detecting the clamp 63 is open or open for another predetermined duration of time, the flush module 76 may be configured to stop and/or reset the timer 86. In some embodiments, the flush module 76 may be configured to stop the timer 86 only after the clamp 63 has been open for the other predetermined duration of time to prevent opening of the clamp 63 when adequate flushing could not have occurred.

In some embodiments, in response to the acoustic sensors 84 detecting the clamp is open for the other predetermined duration, the flush module 76 may be configured to stop the alert at the clamp 63 or provide a different alert at the clamp. Additionally or alternatively, in some embodiments, in response to the acoustic sensors 84 detecting the clamp is open for the other predetermined duration, the flush module 76 may be configured to transmit another alert signal over the network 78 to the clinician monitoring devices 73 to stop the alert or provide a different alert. In some embodiments, the flush module 76 may be configured to provide another indication in the electronic health record 88 of the patient in response to the acoustic sensor 88 detecting the clamp 63 is open for the other predetermined duration of time.

In some embodiments, in response to one or more of the acoustic sensors 84 detecting fluid flowing through the extension tube of the catheter assembly, the flush module 76 may be configured to stop and/or reset the timer 86. In some embodiments, an external server may include one or more components of the computing system 64. For example, the external server may include the processor 66. In some embodiments, the external server may be connected to the clamp 63 and/or the clinician monitoring device 73 via the network 78 or another network. Modifications, additions, or omissions may be made to the FM system 62 without departing from the scope of the present disclosure.

Figure 4A:
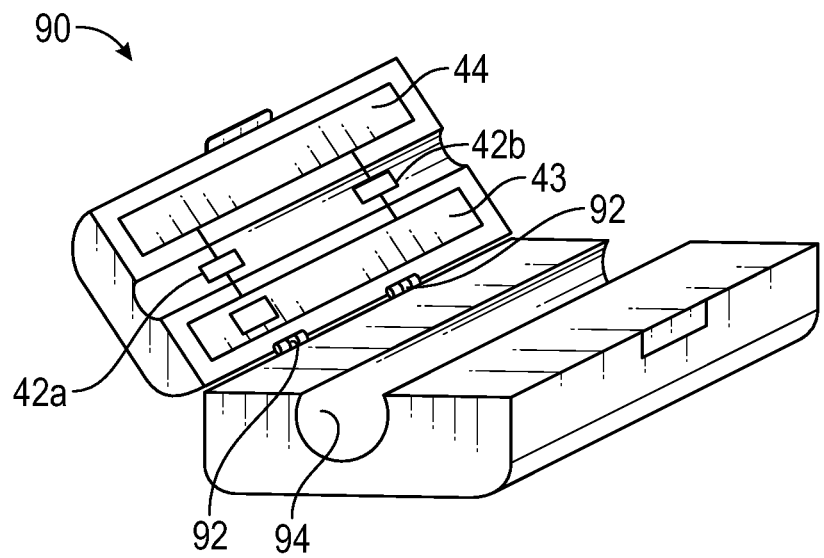
FIG. 4A is an upper perspective view of another example clamp that may be used with the catheter system of FIG. 1A, illustrating the clamp in an open position.
Figure 4B:
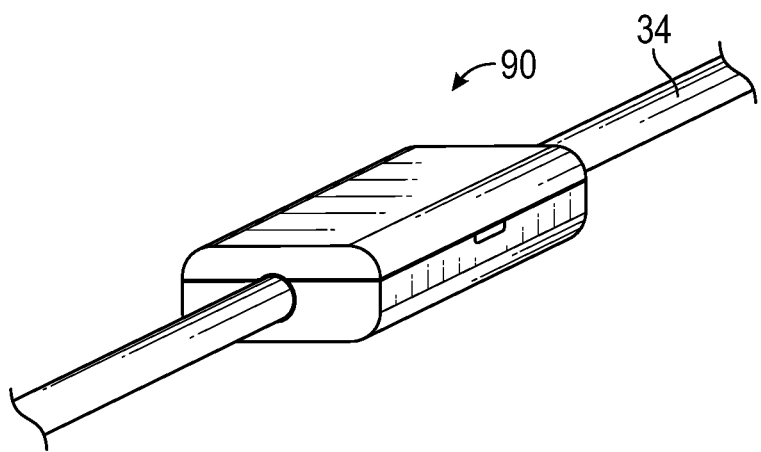
FIG. 4B is an upper perspective view of the clamp of FIG. 4A, illustrating the clamp in a closed position.

Referring now to FIGS. 4A-4B, a clamp 90 is illustrated, according to some embodiments. In some embodiments, the clamp 90 may include or correspond to the clamp 36 described with respect to FIG. 1. In some embodiments, the clamp 90 may replace the clamp 36 in FIG. 1. In some embodiments, the extension tube 34 of the catheter system 14 of FIG. 1 may extend through the clamp 90.

In some embodiments, the clamp 90 may not include a pinch clamp. In some embodiments, the clamp 90 may not be configured to pinch the extension tube 34 or stop fluid flow through the extension tube 34. In some embodiments, when the clamp 90 is disposed in a closed position, the clamp 90 may surround the extension tube 34.

In some embodiments, the extension tube 34 may include the clamp 90 and/or a pinch clamp. In some embodiments, the clamp 90 may be coupled to any suitable extension tube. In some embodiments, the clamp 90 may be disposed on an IV line, which may extend between an IV bag and the catheter assembly 16. In some embodiments, a peripherally inserted central catheter ("PICC") assembly may include pigtail extension tubes, and a particular clamp 90 may be coupled to one or more of the pigtail extension tubes.

In some embodiments, the clamp 90 may open via one or more hinges 92 or another suitable mechanism. In some embodiments, the clamp 90 may include a channel 94 extending there through. In some embodiments, an outer diameter of the extension tube 34 may be slightly less than a diameter of the channel 94. In some embodiments, the extension tube 34 may contact the channel 94.

In some embodiments, a position of the acoustic sensors 42 may vary. In some embodiments, the acoustic sensors 42 may be embedded in the channel 94. In some embodiments, the acoustic sensors 42 may contact the extension tube 34 when the clamp 90 is in the closed position, illustrated, for example, in FIG. 4B. In some embodiments, the acoustic sensors 42 may be spaced apart from the extension tube 34 when the clamp 89 is in the closed position.

In some embodiments, the first acoustic sensor 42a and the second acoustic sensor 42b may provide a robust determination of whether fluid is flowing through the extension tube 34 and the clamp 36 is open or closed. In some embodiments, the first acoustic sensor 42a may be disposed distal to the second acoustic sensor 42b. In some embodiments, a fluid flow direction within the extension tube 34 may be determined in response to the first acoustic sensor 42a detecting fluid flowing through the extension tube 34 prior to or after the other acoustic sensor 42b detecting fluid flowing through the extension tube 34. In some embodiments, the fluid flow direction may be determined to be proximal in response to the first acoustic sensor 42a detecting fluid flowing through the extension tube 34 prior to the second acoustic sensor 42b. In some embodiments, the fluid flow direction may be determined to be distal in response to the second acoustic sensor 42b detecting fluid flowing through the extension tube 34 prior to the first acoustic sensor 42a.

In some embodiments, the acoustic sensors 42 may be electrically coupled to a circuit board 43 and a battery 44. In some embodiments, a location of the circuit board 43 and the battery 44 may vary. In some embodiments, the circuit board 43 may include a communication unit.

Figure 5A:
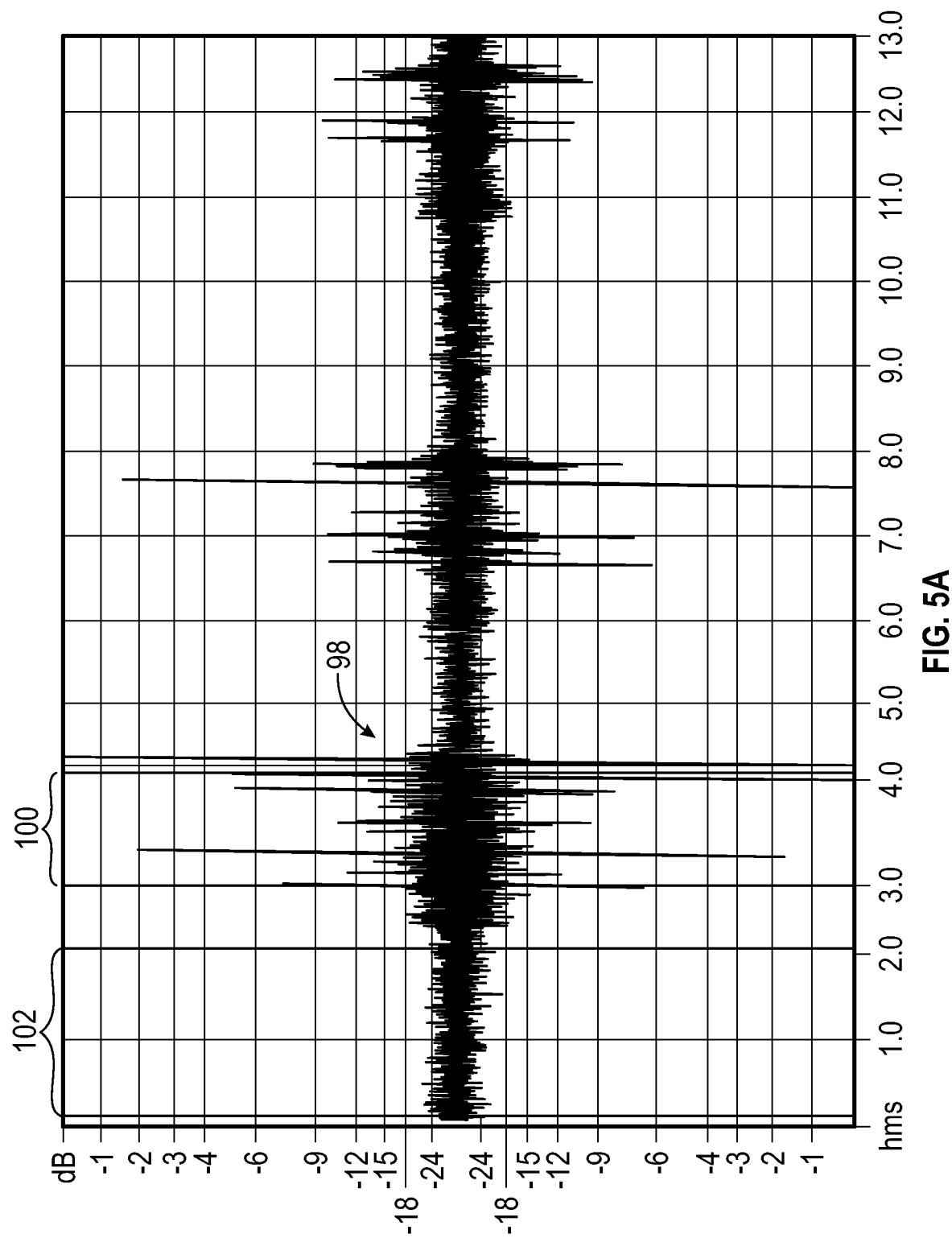
FIG. 5A is a graph of an example waveform generated by an acoustic sensor.

Referring now to FIG. 5A, an example waveform 98 generated by an acoustic sensor is illustrated, according to some embodiments. In some embodiments, a flow portion 100 of the waveform 98 may indicate a fluid flowing through an extension tube, such as, for example, the extension tube 34 described with respect to FIGS. 1 and 2. In some embodiments, a non-flow portion 102 of the waveform 98 may indicate fluid is not flowing through the extension tube 34 or a clamp is closed.

In some embodiments, fluid flow through the extension tube may be determined based on presence of the flow portion 100, which may have a distinct signature, including one or more of the following: a characteristic frequency, a characteristic amplitude, duration, and a characteristic sound energy. In further detail, in some embodiments, the distinct signature of the flow portion 100 may include a characteristic frequency, such as, for example, a maximum or peak frequency, multiple occurrences of the maximum or peak frequency over a duration of time, or an average frequency over a duration of time. Additionally or alternatively, in some embodiments, the distinct signature of the flow portion 100 may include a characteristic amplitude, such as, for example, a maximum or peak amplitude, multiple occurrences of the maximum or peak amplitude over a duration of time, or an average amplitude over a duration of time. In some embodiments, one or more of the following of the distinct signature of the flow portion 100 may be greater or equal to one or more threshold values: the characteristic frequency, the characteristic amplitude, and the characteristic sound energy. In some embodiments, amplitudes or frequencies unrelated to fluid flow, such as, for example, human speaking or alerts, may be filtered out.

In some embodiments, the threshold values may be dependent on one or more of the following: a thickness of a wall of the extension tube, a distance of the acoustic sensor from the extension tube, a material from which the extension tube is constructed, and a gauge size of the extension tube and a catheter, such as, for example the catheter 20 described with respect to FIG. 1. In further detail, in some embodiments, the threshold values may vary based on properties of the extension tube, such as, for example, the thickness of the wall of the extension tube, the material from which the extension tube is constructed, the gauge size of the extension tube, etc. In some embodiments, the threshold values may be measured prior to insertion of the catheter into the patient by infusing fluid through the catheter such that fluid flows through the extension tube of the catheter system and is detected by the acoustic sensor.

In some embodiments, lack of fluid flow through the extension tube may be determined based on presence of the non-flow portion 102, which may have a distinct signature, including one or more of the following: another characteristic frequency, another characteristic amplitude, duration, and another characteristic sound energy. In further detail, in some embodiments, the distinct signature of the non-flow portion 102 may include the other characteristic frequency, such as, for example, a maximum frequency, multiple occurrences of the maximum frequency over a duration of time, or an average frequency over a duration of time. Additionally or alternatively, in some embodiments, the distinct signature of the non-flow portion 102 may include the other characteristic amplitude, such as, for example, a maximum amplitude, multiple occurrences of the maximum amplitude over a duration of time, or an average amplitude over a duration of time. In some embodiments, one or more of the following of the distinct signature of the non-flow portion 102 may be less than the threshold values: the other characteristic frequency, the other characteristic amplitude, and the other characteristic sound energy. In some embodiments, amplitudes or frequencies unrelated to fluid flow, such as, for example, human speaking or alerts, may be filtered out.

In some embodiments, in response to the acoustic sensor detecting one or more of the following, it may be determined fluid is flowing through the extension tube: a particular frequency greater than a particular threshold, a particular amplitude greater than a particular threshold, or a particular sound energy greater than a particular threshold value. In some embodiments, the particular frequency may include a maximum or peak frequency, multiple occurrences of the maximum or peak frequency over a duration of time, or an average frequency over a duration of time. In some embodiments, the particular amplitude may include a maximum amplitude, multiple occurrences of the maximum or peak amplitude over a duration of time, or an average amplitude over a duration of time. In some embodiments, the particular sound energy may be based on the sum of potential and kinetic energy densities integrated over a volume of interest.

In some embodiments, in response to the acoustic sensor detecting one or more of the following, it may be determined fluid is not flowing through the extension tube: a particular frequency less than a particular threshold, a particular amplitude less than a particular threshold, or a particular sound energy less than a particular threshold value. In some embodiments, the particular frequency may include a maximum or peak frequency, multiple occurrences of the maximum or peak frequency over a duration of time, or an average frequency over a duration of time. In some embodiments, the particular amplitude may include a maximum or peak amplitude, multiple occurrences of the maximum or peak amplitude over a duration of time, or an average amplitude over a duration of time.

As illustrated in FIG. 5A, in some embodiments, the maximum amplitude in the non-flow portion 102 may be between about −18 dB and about −24 dB, which may be used as threshold value. In these and other embodiments, the maximum amplitude the flow portion 100 may be higher, such as, for example, about 0 dB, about −2 dB, or about −5 dB, which may be used as threshold values. In some embodiments, the flow portion 100 may correspond to a frequency between about 80 and about 200 Hz, which may be used as threshold values. In some embodiments, the non-flow portion 102 may correspond to a frequency between about 40 and about 80 Hz, which may be used as threshold values. In some embodiments, the waveform 98 of FIGS. 5A-5B may correspond to standard plastic extension tube, such as, for example, that of the Becton Dickinson NEXIVA™ Closed IV Catheter System or a similar catheter system, with the acoustic sensor placed proximate or in close proximity to the extension tube. It is understood that various scales may be used, including seconds, milliseconds, microseconds, or another time unit on the x-axis, and decibels or another unit on the y-axis.

Figure 5B:
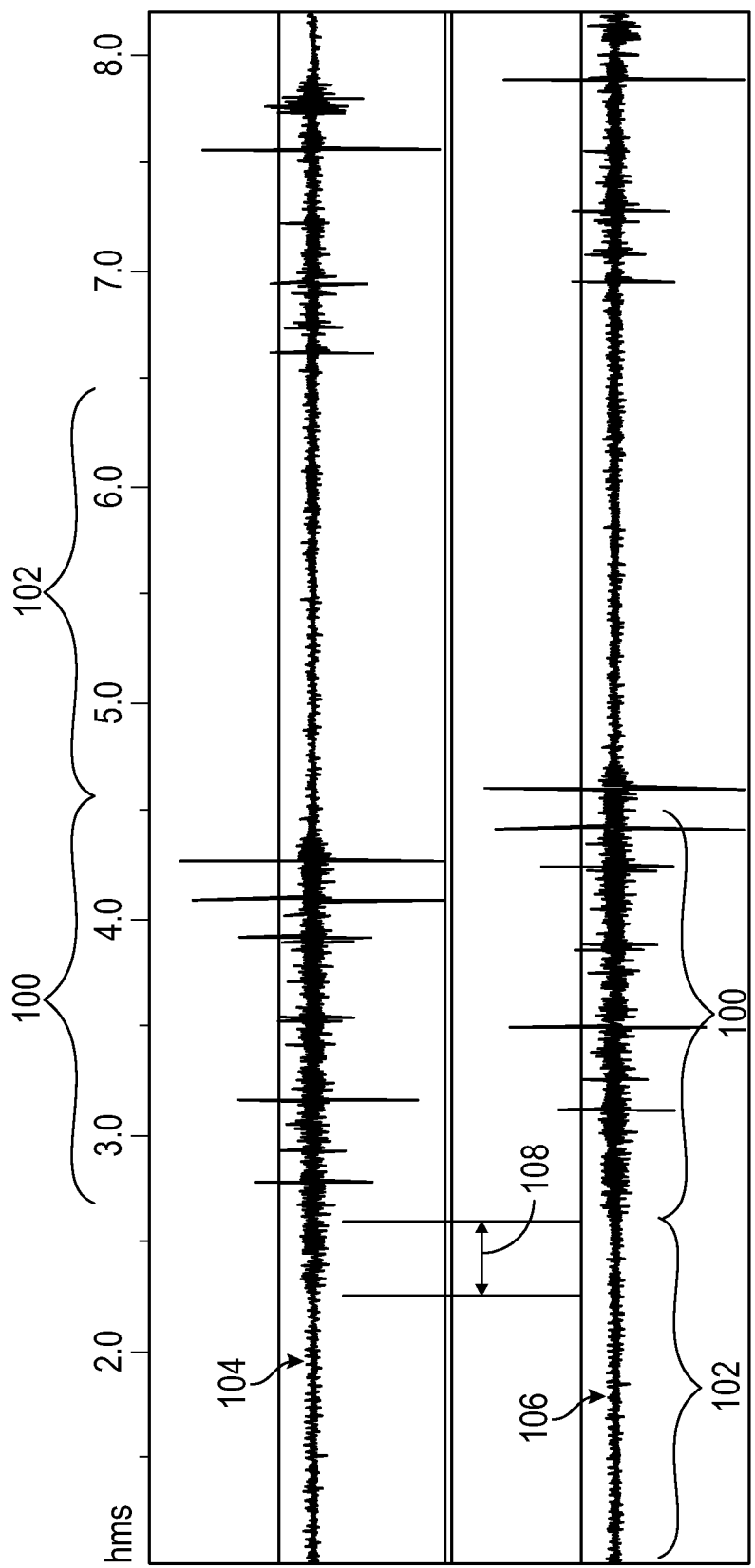
FIG. 5B is a graph of example waveforms generated by two acoustic sensors.

Referring now to FIG. 5B, an example waveform 104 generated by a first acoustic sensor and an example waveform 106 generated by a second acoustic sensor are illustrated, according to some embodiments. In some embodiments, the first acoustic sensor may be disposed distal or proximal to the second acoustic sensor.

In some embodiments, a fluid flow direction within an extension tube, such as, for example, the extension tube 34 described with respect to FIGS. 1 and 2, may be determined in response to the first acoustic sensor detecting fluid flowing through the extension tube prior to or after the other acoustic sensor detecting fluid flowing through the extension tube. As illustrated in FIG. 5B, for example, the first acoustic sensor may detect fluid flowing through the extension tube prior to the second acoustic sensor detecting fluid flowing through the extension tube, as indicated by the flow portion 100 of the waveform 104 occurring earlier in time than the flow portion 100 of the waveform 106. In some embodiments, the flow portion 100 of the waveform 104 may be spaced apart from the flow portion 100 the waveform 106 by a time delay 108.

In some embodiments, in response to the first acoustic sensor being disposed distal to the second acoustic sensor, the time delay 108 illustrated in FIG. 5B may indicate fluid flowing through the extension tube in a proximal direction. In some embodiments, in response to the first acoustic sensor being disposed proximal to the second acoustic sensor, the time delay 108 illustrated in FIG. 5B may indicate fluid flowing through the extension tube in a distal direction.

Again, it is understood that various scales may be used, including seconds, milliseconds, microseconds, or another time unit on the x-axis, and decibels or another unit on the y-axis. In some embodiments, the time delay 108 may be less than one or more milliseconds or less than one or more microseconds. In some embodiments, the time delay 108 may be based on a distance between the first acoustic sensor and the second acoustic sensor, which may vary. In some embodiments, the first acoustic sensor and/or the second acoustic sensor may detect a distance or time delay between one or more peaks of the waveform 104 and the waveform 106, which may indicate fluid flowing through the extension tube in a particular direction. For example, if the first acoustic sensor detects one or more peaks prior to the second acoustic sensor detecting the one or more peaks, it may be determined that fluid is flowing in the proximal direction.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A pinch clamp for an extension tube coupled to a catheter adapter, the pinch clamp comprising:
   a first arm having a protrusion forming a clamping surface;
   a second arm opposing the first arm, wherein distal ends of the first arm and the second arm are connected via a hinge, and wherein proximal ends of the first arm and second arm are selectively engageable to cause the protrusion to clamp an extension tube positioned between the first and second arms;
   a first microphone embedded in the second arm;
   a second microphone embedded in the second arm proximal to the first microphone;
   a light; and
   a computing system that is configured to:
      detect, from signals received from the first and second microphones, that fluid is not flowing within the extension tube;
      in response to detecting that fluid is not flowing within the extension tube, start a timer for a predetermined amount of time;
      in response to the timer elapsing, causing the light to provide an indication on the pinch clamp that fluid has not flowed through the extension tube for the predetermined amount of time;
      detect, from signals received from the first and second microphones, that fluid is flowing in a distal direction within the extension tube; and
      in response to detecting that fluid is flowing in the distal direction within the extension tube, ceasing to cause the light to provide the indication.

2. The pinch clamp of claim 1, wherein the light is embedded in the first arm.

3. The pinch clamp of claim 1, wherein the computing system is embedded in the second arm.

4. The pinch clamp of claim 1, wherein the computing system is configured to cause the light to provide a prior indication on the pinch clamp in response to a second amount of time elapsing, the second amount of time being less than the predetermined amount of time.

5. The pinch clamp of claim 4, wherein the prior indication and the indication are different colors.

6. The pinch clamp of claim 4, wherein the prior indication and the indication are different blinking rates or patterns.

7. The pinch clamp of claim 1, wherein the computing system is configured to transmit information representing the detection that fluid is not flowing within the extension tube and the detection that fluid is flowing in the distal direction within the extension tube.

8. The pinch clamp of claim 7, wherein the information includes a time of each detection.

9. The pinch clamp of claim 1, wherein the computing system detects, from signals received from the first and second microphones, that fluid is flowing in the distal direction within the extension tube by determining that the second microphone generated a signal indicative of fluid flow before the first microphone generated a single indicative of fluid flow.

10. The pinch clamp of claim 9, wherein the computing system identifies the signal indicative of fluid flow by determining that the respective signal has an amplitude greater than a threshold.

11. The pinch clamp of claim 10, wherein the amplitude is an average amplitude.

12. The pinch clamp of claim 10, wherein the threshold is based on a thickness of the extension tube.

13. The pinch clamp of claim 1, wherein the first and second microphones are at a surface of the second arm such that the first and second microphones contact the extension tube.

14. A pinch clamp for an extension tube coupled to a catheter adapter, the pinch clamp comprising:
   a first arm having a protrusion forming a clamping surface;
   a second arm opposing the first arm, wherein distal ends of the first arm and the second arm are connected via a hinge, and wherein proximal ends of the first arm and second arm are selectively engageable to cause the protrusion to clamp an extension tube positioned between the first and second arms;
   a first microphone embedded in the second arm;
   a second microphone embedded in the second arm proximal to the first microphone; and a computing system for detecting, from signals from the first and second microphones, whether fluid is flowing within the extension tube.

\* \* \* \* \*